United States Patent
Makiyama et al.

(10) Patent No.: US 7,929,136 B2
(45) Date of Patent: Apr. 19, 2011

(54) MIST MEASURING APPARATUS

(75) Inventors: Tadashi Makiyama, Fukuyama (JP); Takuya Kawamoto, Fukuyama (JP); Yasuo Yamane, Higashihiroshima (JP); Katsuhiko Sekiya, Higashihiroshima (JP)

(73) Assignee: Horkos Corporation, Hiroshima (JP)

( * ) Notice: Subject to any disclaimer, the term of this patent is extended or adjusted under 35 U.S.C. 154(b) by 82 days.

(21) Appl. No.: 12/532,097

(22) PCT Filed: Sep. 19, 2007

(86) PCT No.: PCT/JP2007/001012
§ 371 (c)(1), (2), (4) Date: Sep. 18, 2009

(87) PCT Pub. No.: WO2008/114325
PCT Pub. Date: Sep. 25, 2008

(65) Prior Publication Data
US 2010/0103415 A1    Apr. 29, 2010

(30) Foreign Application Priority Data
Mar. 19, 2007 (JP) .................................. 2007-070606

(51) Int. Cl.
*G01N 21/00* (2006.01)
(52) U.S. Cl. ........................................................ 356/337
(58) Field of Classification Search ........................ None
See application file for complete search history.

(56) References Cited

U.S. PATENT DOCUMENTS

| | | | |
|---|---|---|---|
| 5,255,089 A | 10/1993 | Dybas et al. | |
| 6,618,144 B1 * | 9/2003 | Reed | 356/343 |
| 7,187,441 B1 * | 3/2007 | Sevick-Muraca et al. | 356/336 |
| 2006/0171788 A1 | 8/2006 | Doerr et al. | |

FOREIGN PATENT DOCUMENTS

| | | |
|---|---|---|
| JP | 6-82358 A | 3/1994 |
| JP | 2000-141162 A | 5/2000 |
| JP | 2003-53644 A | 2/2003 |
| JP | 2005-91061 A | 4/2005 |

OTHER PUBLICATIONS

Makiyama et al., "Visualizing and Measuring of Splayed Mixture with Optical Dispersion Method for MQL Drilling", The Japan Society for Precision Engineering, Sep. 4, 2006, pp. 453-454.
Makiyama et al., "Effects of MQL on Drilling (1st Report)", Journal of the Japan Society of Precision Engineering, vol. 73, No. 2, Feb. 15, 2007, pp. 232-236.

* cited by examiner

*Primary Examiner* — Tu T Nguyen
(74) *Attorney, Agent, or Firm* — Birch, Stewart, Kolasch & Birch, LLP (57) ABSTRACT

An object of the present invention is to provide a mist measuring apparatus in which visual confirmation performance is enhanced, and high-accuracy detection is enabled. In the mist measuring apparatus including a housing, and a light source that is provided in this housing and emits light to a misty cutting fluid, the housing is provided around an ejection part of the misty cutting fluid, the light emitted from the light source is a visible ray, and the housing is provided with an observation part for observing scattered light from the misty cutting fluid.

6 Claims, 7 Drawing Sheets

| PUMP | PLUNGER PUMP (DRIVEN WITH PNEUMATIC CYLINDER) OPERATION FREQUENCY: 0.2Hz, 0.5Hz, 1Hz, 1.5Hz, 2Hz, 2.5Hz, 3Hz, 4Hz, 4.2Hz CAPACITY  SMALL PUMP : 0.8mm³/stroke   MEDIUM PUMP: 4.2mm³/stroke   LARGE PUMP : 20.6mm³/stroke |
|---|---|
| CUTTING FLUID | COMPONENTS : POLYOLESTER VISCOSITY: 19.1mm²/s (40°C) DENSITY: 0.95g/cm³ (15°C) |
| DRILL | MATERIAL : TiN-COATED CEMENTED CARBIDE TWIST DRILL WITH TWO OIL HOLES DIAMETER : 6.8mm  LENGTH : 109mm |
| MACHINE | SPINDLE ROTATION SPEED: 5617rpm, 0rpm AIR SOURCE: 0.5Mpa |
| LIGHT SOURCE | LIGHT-EMITTING DIODE (WAVELENGTH: 520nm) |

FIG. 7

ONLY AIR (WITHOUT MIST)

MIST MEASURING APPARATUS

TECHNICAL FIELD

The present invention relates to a mist measuring apparatus, and more particularly to a mist measuring apparatus in which a misty cutting fluid for use in a machine tool can be visually measured, and a mist measuring apparatus in which a mist quantity can be automatically measured.

BACKGROUND ART

In a machine tool, for example, when an automobile part is subjected to cutting machining, a cutting fluid is supplied, and there is a method of MQL (Minimum Quantity Lubrication), which reduces a quantity of this cutting fluid to a necessary minimum. When the misty cutting fluid is supplied by the MQL, the quantity of the used cutting fluid is smaller, which brings about various advantages such as decrease in environmental load and reduction in cost. Accordingly, in the MQL, it is preferable that the supplied quantity of the cutting fluid is as small as possible.

On the other hand, it is preferable to sufficiently supply the cutting fluid in view of tool life and machining accuracy. Therefore, during machining by the MQL, the misty cutting fluid (hereinafter, the misty cutting fluid is referred to as "mist") needs to be supplied efficiently and stably in the vicinity of a tool and at a portion where the tool and a workpiece come into contact with each other.

For this purpose, a state and a quantity of the mist ejected from oil holes in the vicinity of the tool, for example, oil holes provided in a drill itself need to be automatically measured and fed back to the machine tool to eject the mist without excess and deficiency.

In this case, it is convenient to visually confirm the quantity of the mist by the human eye, so that the ejection state of the mist can be checked at a glance.

However, the quantity of the mist, which is very small, cannot be visually confirmed as it is. Even if the ejected quantity of the cutting fluid is measured by a scale on a clear tube in which the cutting fluid is stored before the ejection, fine detection cannot be performed because of a very small consumed quantity of the mist. Moreover, when there occurs an ejection failure such as liquefaction of the mist, a reduction in the mist quantity in the clear tube and an actual mist quantity do not coincide with each other.

Furthermore, in view of automatization of a cutting machining facility, it is expected to automatically detect the quantity of the mist and automatically adjust the quantity of the mist based on this detected quantity so as to prevent the ejection failure.

Patent Literature 1 proposes a method for controlling a quantity of coolant in which a magnetic sensor is disposed in an outer peripheral portion of a body made of a non-magnetic material and a passage of a coolant is provided inside the body, so that a flow state of the misty coolant containing a magnetic fluid is detected by the magnetic sensor to control a quantity of the coolant based on this detected output.

Patent Literature 2 proposes an apparatus that optically detects a proportion of aerosol (mist), and gravimetrically detects a flow rate of a lubricant film precipitated inside the passage through which the aerosol passes to thereby measure the aerosol and the flow rate of the lubricant in the precipitated state, separately. In this optical sensor, there are two types: one is a type in which appropriate light is directed to the flow of the aerosol inside the measuring apparatus, and the other is a type in which an air flow is produced from the measuring apparatus to the optical sensor, and the aerosol is carried by the air flow.

Patent Literature 3 proposes a lubricant-ejection-state detecting apparatus for machine tool in which light of a projector is projected to an ejection point of a misty lubricant to detect a transmissivity determined by concentration of an ejection state in a light receiver, and a lubricant-ejection-state detecting apparatus for machine tool in which light of a projector is projected to an ejection point of a misty lubricant to detect reflected light from the misty lubricant in a light receiver. In each of these apparatuses, since the transmitted light or the reflected light of the misty cutting fluid is received by the light receiver, the projector, the ejection point and the light receiver are linearly located.

CITATION LIST

Patent Literature

Patent Literature 1: Japanese Laid-Open Patent Publication No. 2000-141162
Patent Literature 2: U.S. Laid-Open Patent Publication No. US2006/0171788A1
Patent Literature 3: Japanese Laid-Open Patent Publication No. 2003-53644

SUMMARY OF INVENTION

Technical Problems

However, in the detector of the coolant described in Patent Literature 1, since the coolant is composed of misty, extremely fine particles, the coolant cannot be visually observed.

Moreover, since the coolant needs to contain a magnetic substance (magnetic particles), working processes are increased in number, and further, a cost is increased. Furthermore, containing the magnetic substance decreases detection accuracy and cutting accuracy at the time of metal machining, above all when a magnetic body is machined. For example, when a workpiece is a magnetic body, magnetic force acts between the coolant and the metal, and thus, a flow of the cutting fluid becomes worse or stagnant. Even if the magnetic particles contained in the cutting fluid are detected using the magnetic sensor in this state, temporal variation in ejected quantity cannot be detected.

In the lubricant measuring apparatus described in Patent Literature 2, since directionality of a laser is too high, a beam is outputted only in a narrow range. For example, in the case of a relatively inexpensive semiconductor laser, a wavelength is relatively long, which makes visual confirmation impossible or even if not, it is very hard to observe the light. Accordingly, in this lubricant measuring apparatus, it is substantially impossible to directly observe the whole ejection state of the optical aerosol.

Furthermore, while the optical sensor is utilized to measure the quantity of the lubricant, in the type in which the appropriate light is directed to the flow of the aerosol inside the measuring apparatus, a direction of the light is varied. Thus, the ejection state of the whole aerosol cannot be detected.

In the type in which the air flow is produced from the measuring apparatus to the optical sensor to carry the aerosol by the air flow, the aerosol is precipitated or the direction thereof is changed during a carriage by the air flow, and direct measurement at a contact portion between a tool and a workpiece is impossible. Moreover, in the gravimetry, although the quantity of the precipitated aerosol can be measured, temporal variation in the ejection state is hardly grasped.

The applicant in Patent Literature 3 is partially common to the applicants of the present invention. The present invention provides a mist measuring apparatus in which a different detection method from that of the invention described in Patent Literature 3 is used to enable the visual confirmation of the ejection state of the mist, and the detection of the misty lubricant in the optical sensor is improved.

In Patent Literature 3, while the projector, the ejection point and the light receiver are linearly located to measure the transmitted light or the reflected light at the ejection point, the light does not necessarily advance in one direction when the light is projected to the misty cutting fluid.

In many cases, once the light enters the misty cutting fluid, the light reflects multidirectionally due to particles of the mist instead of reflecting in one direction or transmitting, and this reflection is repeated among the particles many times. Namely, once the light enters the misty cutting fluid, the light is scattered. Accordingly, measuring the scattered light is more effective in detecting a very small quantity of light than measuring the reflected light or the transmitted light. Moreover, even if the mist is tried to be observed by the transmitted light or the reflected light, the light advancing from the projector to the mist enters eyes, which makes it difficult to conduct the direct visual confirmation.

In view of the above-described situation, an object of the present invention is to provide a mist measuring apparatus in which visual confirmation performance of a misty cutting fluid is enhanced by visually observing scattered light, a high-accuracy mist measuring apparatus in which the scattered light can be detected by an optical sensor, and a mist measuring apparatus in which the visual confirmation performance is enhanced and the scattered light can be detected with high accuracy by an optical sensor.

Solution to Problems

In order to achieve the above-described object, the present invention takes the following technical measures.

According to a first aspect of the present invention, in a mist measuring apparatus including a housing, and a light source that is provided in the housing and emits light to a misty cutting fluid, the housing is provided around an ejection part of the misty cutting fluid, the light of the light source is a visible ray, and the housing is provided with an observation part for observing scattered light from the misty cutting fluid.

With this configuration, the light emitted from the light source is scattered in the mist, and the scattering state can be visually observed. In this case, since the housing blocks off outside light, and the light is a visible ray, when the scattered light of the mist is observed through the observation part provided in this housing, the scattered light seems to pop up in a dark room, so that a quantity and a state of the mist can be visually confirmed.

That is, since the cutting fluid is misty, the light emitted from the light source repeats irregular reflection many times among the particles of the mist and is scattered. Accordingly, by viewing this scattered light, the ejection state of the mist can be visually observed.

Moreover, since viewing the scattered light prevents the outgoing light from the light source from directly entering eyes, it is easy to visually confirm the ejection state.

In the mist measuring apparatus according to the first aspect of the present invention, it is more preferable that a wavelength of the light emitted from the light source is not less than 490 nm and not more than 550 nm.

With this configuration, since a wavelength of substantially green light, which is more favorable in visual confirmation performance among visible rays, is utilized, it is possible to visually confirm the ejection state more clearly.

In the mist measuring apparatus according to the first aspect of the present invention, it is preferable that a cylindrical reflection preventer whose inner surface is a reflecting surface is provided in an optical path from the light source to the misty cutting fluid.

With this configuration, the light from the light source to the mist is not curved toward the observation part, so that it is hard for the light from the light source to be directly confirmed visually at the observation part. Moreover, the light is efficiently emitted to the mist, which enhances the visual confirmation performance of the ejection state of the mist.

According to a second aspect of the present invention, a mist measuring apparatus includes a housing, a light source that is provided in the housing and emits light to a misty cutting fluid, and an optical sensor that is provided in the housing and receives light from the misty cutting fluid to measure an ejected quantity of the misty cutting fluid based on a quantity of received light of the optical sensor, the optical sensor receives scattered light from the misty cutting fluid, and the housing is provided around an ejection part of the misty cutting fluid.

Receiving the scattered light by the optical sensor in this manner allows the mist quantity to be detected.

That is, instead of the reflected light and the transmitted light, the scattered light is detected. Moreover, blocking off the outside light by the housing provided around the mist ejection part makes the sensitivity of the sensor high.

In this case, when the wavelength of the light source is shortened, the energy of the outgoing light from the optical source is increased. Accordingly, energy of the scattered light in the mist is also increased, and the sensitivity in the optical sensor is enhanced, which enables the mist quantity to be observed with high accuracy. Moreover, the light having a wavelength which makes the visual confirmation easier allows the ejection state of the mist to be visually checked.

In the mist measuring apparatus according to the second aspect of the present invention, it is preferable to include a mist adjusting part that automatically adjusts a quantity of the misty cutting fluid to be ejected in accordance with the ejected quantity measured by the optical sensor.

With this configuration, since the quantity of mist to be ejected is adjusted based on the light quantity measured by the optical sensor, that is, based on the mist quantity, the automatization of the MQL is enabled, resulting in laborsaving and reduction in cost.

In the mist measuring apparatus according to the second aspect of the present invention, it is preferable that a plurality of optical sensors are provided.

With this configuration, the light quantity of the scattered light detectable from the mist is increased, so that accuracy of the mist measuring apparatus is enhanced. Moreover, the multidirectional detection reduces the possibility that the light is blocked off by the tool, thereby making the detected scattered light smaller, and allows the state of the mist to be more specifically measured from multiple directions.

In the mist measuring apparatus according to the second aspect of the present invention, it is preferable that a cylindrical reflection preventer whose inner surface is a reflecting surface is provided in an optical path from the light source to the misty cutting fluid, and that a collecting lens is provided in an optical path from the misty cutting fluid to the optical sensor.

Since the reflection preventer is provided as described above, the light from the light source does not curve toward the optical sensor, and thus, less light from the light source to the misty cutting fluid directly enters the optical sensor. Moreover, since the light is efficiently emitted to the mist, the sensitivity of the detection of the mist is enhanced.

Furthermore, since the collecting lens is provided in the optical path from the mist to the optical sensor, the scattered light from the mist is collected and enters the optical sensor, which enhances the sensitivity of the optical sensor, and allows the state of the mist to be detected with high accuracy.

In the mist measuring apparatus according to the second aspect of the present invention, a wavelength of the light source may be not more than 490 nm.

With this configuration, since the light having a wavelength of not more than 490 nm has strong energy, the sensitivity of the optical sensor is enhanced, and electrical detection accuracy in the optical sensor is enhanced.

In the mist measuring apparatus according to the second aspect of the present invention, the light of the light source may be a visible ray, and the housing may be provided with an observation part for observing the scattered light from the misty cutting fluid.

With this configuration, since the light of the light source is a visible ray, the state of the mist can be visually confirmed through the observation part.

In the mist measuring apparatus according to the second aspect of the present invention, the light source may include a light source having a wavelength of less than 490 nm and a light source having a wavelength of not less than 490 nm and not more than 810 nm, and the housing may be provided with an observation part for observing the scattered light from the misty cutting fluid.

In this manner, when the light sources having the different wavelengths are provided and these light sources of two wavelengths are used in combination, the light having a wavelength of less than 490 nm has strong energy, since the shorter the wavelength is, the higher the energy of the light is. Therefore, the sensitivity of the optical sensor is enhanced, and the electrical detection accuracy in the optical sensor is enhanced.

Moreover, since the light having a wavelength of not less than 490 nm and not more than 810 nm, which is, for example, green, yellow or the like, is excellent in visual confirmation performance under a dark room, that is, against a black ground, the visual confirmation performance of the mist is enhanced.

In the mist measuring apparatus according to the second aspect of the present invention, the light source may include a light source having a wavelength of less than 490 nm and a light source having a wavelength of not less than 490 nm and not more than 550 nm, and the housing may be provided with an observation part for observing the scattered light from the misty cutting fluid.

In this manner, when the light sources having the different wavelengths are provided and these light sources of two wavelengths are used in combination, the light having a wavelength of less than 490 nm has strong energy, so that the sensitivity of the optical sensor is enhanced, and the electrical detection accuracy in the optical sensor is enhanced. And further, the light having a wavelength of not less than 490 nm and not more than 550 nm is especially excellent in visual confirmation performance, thereby enabling clearer observation.

As described above, the use of the lights of two wavelengths in combination can realize the mist measuring apparatus with favorable sensitivity in the optical sensor, and high visual confirmation performance.

In this case, the two light sources having the different wavelengths may be used simultaneously, or the light sources may be switched to be used as needed.

In the mist measuring apparatus according to the present invention, it is preferable that a light-emitting diode is used for the light source.

With this configuration, since the light-emitting diode can emit light having various wavelengths, the light having a wavelength of less than 490 nm, and the light having a wavelength of not less than 490 nm and not more than 550 nm as described above can be emitted. Moreover, since the light-emitting diode has a fast response speed, follow-up of the automatic control can also be performed fast. Furthermore, the price is lower, and adequate directionality for illuminating the whole mist is provided.

Advantageous Effects of Invention

According to the present invention, it is possible to obtain a mist measuring apparatus in which visual confirmation performance of a misty cutting fluid is enhanced by visually observing scattered light, a high-accuracy mist measuring apparatus in which the scattered light can be detected by an optical sensor, and a mist measuring apparatus in which the visual confirmation performance is enhanced and the scattered light can be detected with high accuracy by an optical sensor.

DESCRIPTION OF EMBODIMENTS

Hereinafter, embodiments of the present invention will be described with reference to the drawings.

Figure 1:
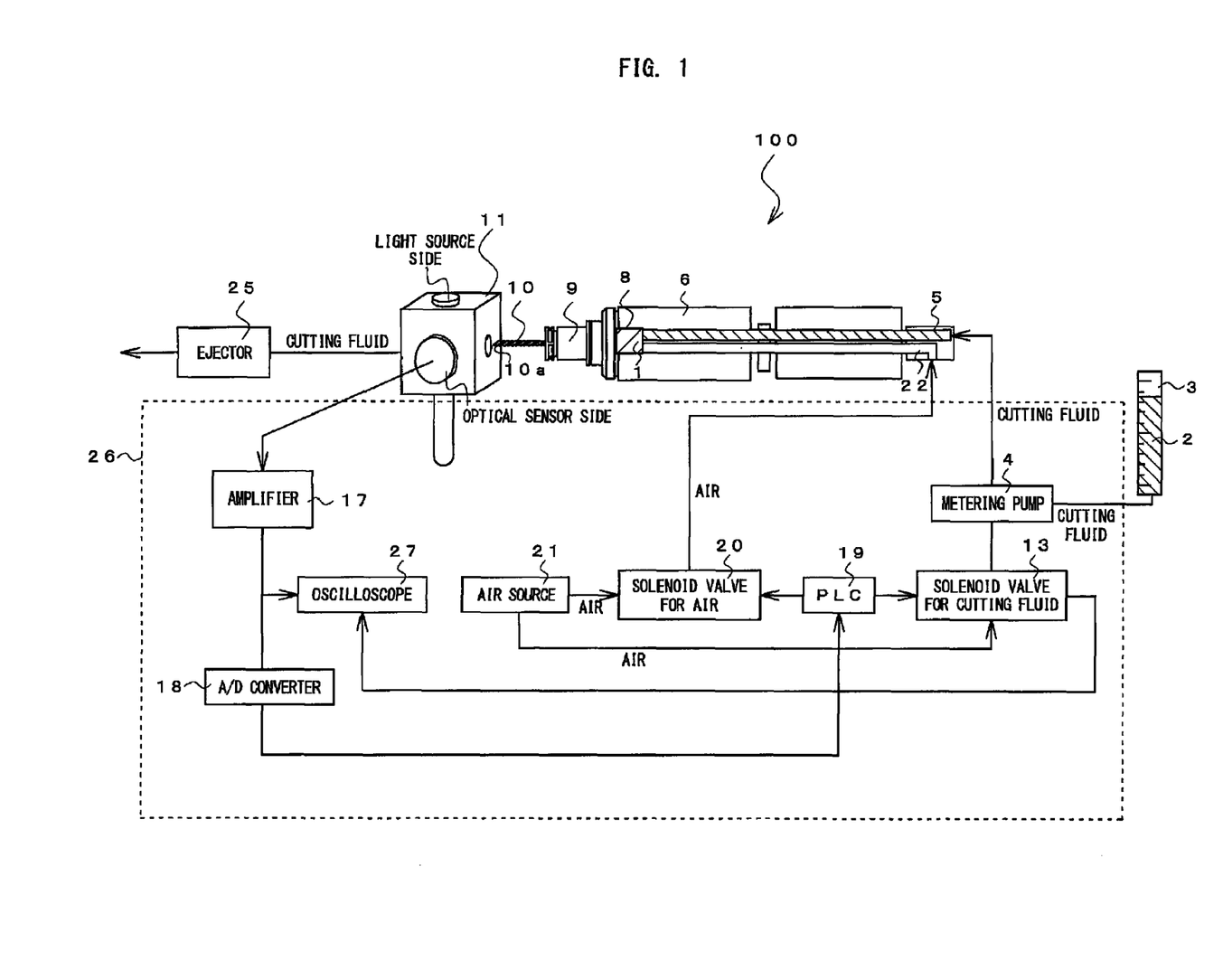
FIG. 1 is an overall view of a mist measuring apparatus.

FIG. 1 is an overall view of a mist measuring apparatus.

In this mist measuring apparatus 100, a cutting fluid 2 fills a clear tube 3, and this cutting fluid 2 is sent out by a metering pump 4. The metering pump 4 is of a pneumatically-driven plunger type, and discharges the cutting fluid 2 in accordance with an operation of a solenoid valve for cutting fluid 13.

By controlling an operation frequency of the metering pump 4, an ejected quantity of the cutting fluid 2 is adjusted, and by reading a scale provided on the clear tube 3, total consumption of the cutting fluid 2 is obtained. The detection by the scale on this clear tube 3 is performed to measure a total ejected quantity of mist, and this detected quantity is not used to control the mist ejection, which requires the detection of a very small quantity.

Furthermore, this cutting fluid 2 is conveyed through a rotary joint for multi-channel 5 to a mixing nozzle 8 provided in the vicinity of a tool 10 in a front end portion inside a main spindle 6 of a machine tool, which is a rotary side.

Inside the mixing nozzle 8, air 22 and the cutting fluid 2 are mixed to make the cutting fluid 2 misty (hereinafter, the misty cutting fluid 2 is referred to as "mist 1" for convenience).

A front end of the tool 10 is inserted into a mist measuring part 11, and an ejection state and a quantity of the mist 1 are measured inside this mist measuring part 11. A drill is used for the tool 10. The tool 10 is attached to a tool holder 9 so as to be freely replaced by a tool having a different shape. At the front end of the tool 10, an ejection part 10a of the mist 1 is provided.

Figure 2:
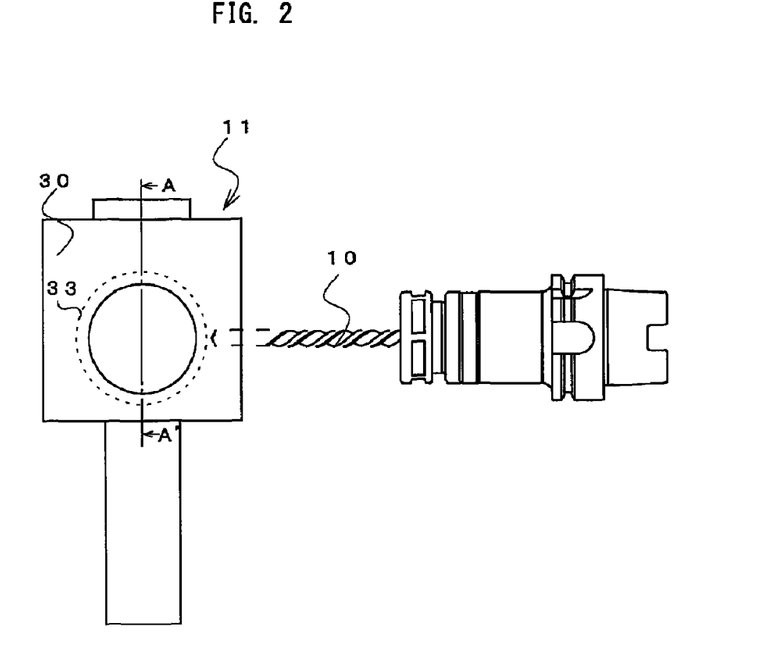
FIG. 2 is a view showing a mist measuring part according to a first embodiment.
Figure 3:
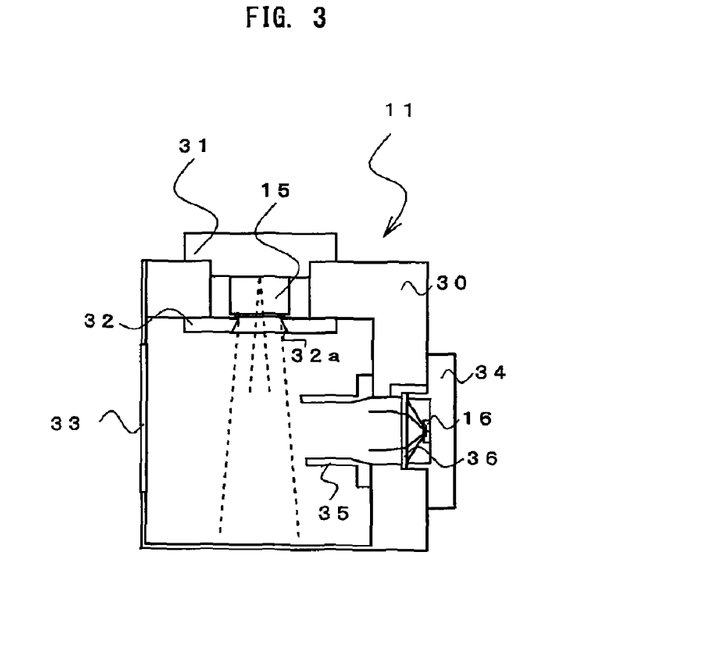
FIG. 3 is a cross-sectional view along line A-A' of FIG. 2.
Figure 4:
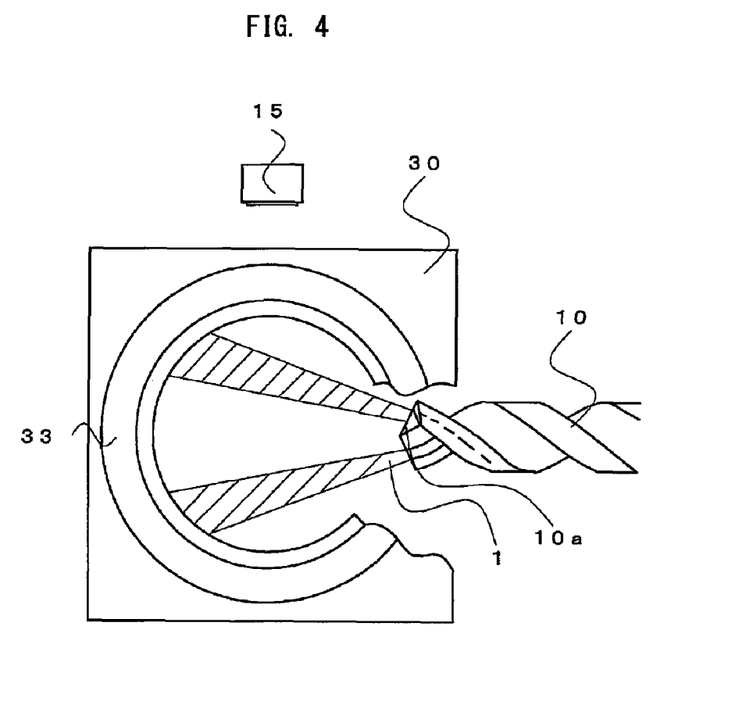
FIG. 4 is a schematic view of an ejection state of mist.

FIG. 2 is a view showing the mist measuring part according to a first embodiment of the present invention, and FIG. 3 is a cross-sectional view along line A-A' of FIG. 2. FIG. 4 is a schematic view of an ejection state of the mist.

As shown in FIGS. 2 and 3, this mist measuring part 11 has a box shape, and is provided with a light-emitting diode 15 serving as a light source in an upper portion inside the box. A phototransistor 16 is provided perpendicularly to both an emission direction of light from the light-emitting diode 15 and an ejection direction of the mist 1 (vertical direction on the paper of FIG. 3).

Moreover, an observation part 33 made of a transparent window is provided on the opposite side of the phototransistor 16 in the mist measuring part 11. Accordingly, the observation part 33 is, similarly to the phototransistor 16, perpendicular to both the emission direction of the light-emitting diode 15 and the ejection direction of the mist 1.

The light emitted from the light-emitting diode 15 is scattered in the mist 1, and the scattered light is detected by the phototransistor 16 to thereby detect the scattered light in the mist 1 in FIG. 1.

Based on a quantity of this obtained scattered light, a quantity of the mist to be ejected is adjusted by a mist adjustment part 26 in FIG. 1.

An analog electric signal from the phototransistor 16 is amplified by an amplifier 17 shown in FIG. 1 and then, goes through an A/D converter 18 to be converted into a digital signal and inputted into a PLC (Programmable Logic Controller) 19. The detected mist 1 is then discharged outside the mist measuring part 11 through an ejector 25 made of a vacuum pump.

In the PLC 19, CNC (Computer Numeral Control) is performed for the mist 1, in which data from the optical sensor is analyzed and converted into a mist quantity. If the mist quantity exceeds a predetermined quantity, or does not satisfy the predetermined quantity, an abnormality message is issued, and a control signal is sent to a solenoid valve for air 20, the solenoid valve for cutting fluid 13 and the metering pump 4 to adjust the mist quantity.

The solenoid valve for air 20 and the solenoid valve for cutting fluid 13 are connected to an air source 21 to each play a role of an electromagnetic valve for compressed air fed from the air source 21.

As described above, the mist measuring apparatus 100 automatically detects the ejection state of the mist 1, and automatically adjusts the quantity to be ejected of the mist 1 in accordance with the detection state.

Hereinafter, the detection of the mist 1 in the mist measuring part 11 will be described in detail.

As shown in FIGS. 3 and 4, the tool 10 is inserted into an insertion opening of the housing 30 in the mist measuring part 11, and the mist 1 is sprayed from the ejection part 10a at the front end of this tool 10. The light-emitting diode 15 serving as the light source is attached to the housing 30 by a light-emitting diode fixing part 31, and a reflection preventer 32 that is cylindrical, and an inner surface of which is a reflecting surface 32a is provided in the emission direction of the light of this light-emitting diode 15.

As described above, the transparent window-like observation part 33 is provided in the housing 30 in a direction perpendicular to the light-emitting diode 15 serving as the light source, and the phototransistor 16 serving as the optical sensor is also attached in the direction perpendicular to the light-emitting diode 15. This phototransistor 16 is fixed to the housing 30 by a phototransistor fixing part 34.

Attached to a light receiving path to the phototransistor 16 are a cylindrical light receiving path tube 35 and an aspheric condenser lens 36 which is a collecting lens. The measurement of the mist 1 is performed in the mist measuring part 11 as described above.

Figure 5:
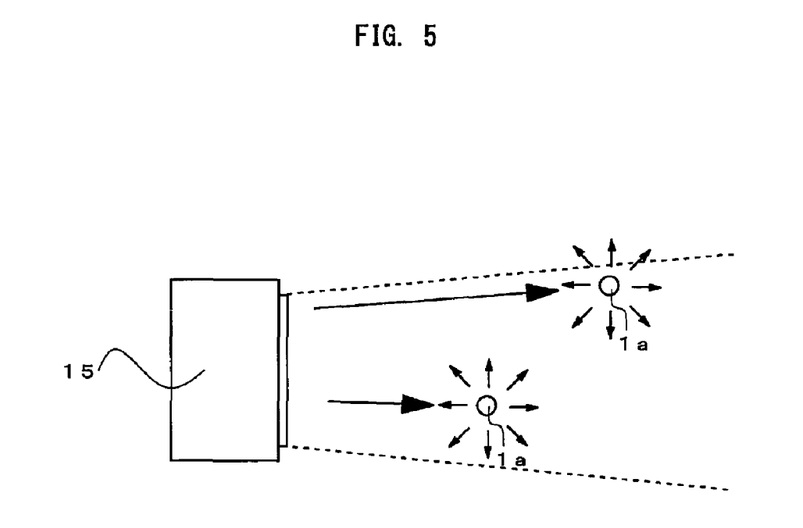
FIG. 5 is a view showing a scattering state in the mist.

First, the outgoing light of the light-emitting diode 15 is emitted toward the mist 1. The outgoing light passes through the reflection preventer 32, and is scattered in the mist 1. FIG. 5 is a view showing a scattering state in the mist.

As shown in FIG. 5, when the light from the light-emitting diode 15 hits particles 1a of the mist 1, the light is scattered. That is, the light reflects in various directions without reflecting in one direction or transmitting, and this irregular reflection is repeated many times among the particles 1a of the mist 1.

Accordingly, observing this scattered light through the observation part 33 allows the ejection state of the mist 1 to be visually confirmed. Since the housing 30 blocks off outside light, an inside of the mist measuring part 11 becomes a dark room, and thus, the ejection state can be visually confirmed more clearly. Moreover, since the observation part 33 is provided perpendicularly to the light source, observation of the light other than the scattered light is reduced.

In this case, when the visual confirmation is emphasized, the light emitted by the light-emitting diode 15 is substantially green if a wavelength thereof is not less than 490 nm and not more than 550 nm, thereby it is easy to visually confirm. Moreover, directionality of the light is adequate and various types of diodes can be selected in accordance with the ejection state.

Furthermore, the scattered light is detected by the phototransistor 16 serving as the optical sensor. In this case, the scattered light from the mist 1 passes through the light receiving path tube 35 and is collected by the aspheric condenser lens 36 and then, is detected by the phototransistor 16. Since the phototransistor 16 is also perpendicular to the outgoing light of the light-emitting diode 15, reception of the light other than the scattered light is reduced.

The reflection preventer 32 has the reflecting surface 32a in the inner surface thereof, and the outgoing light of the light-emitting diode 15 is reflected by this reflecting surface 32a, so that a range of the outgoing light of the light-emitting diode 15 can be adjusted to match the mist 1. Moreover, since the light receiving path tube 35 is provided, the less outgoing light from the light-emitting diode 15 to the mist 1 enters the phototransistor 16. Furthermore, since the incident light to the phototransistor 16 is collected in the aspheric condenser lens 36, sensitivity to the scattered light of the phototransistor 16 is increased, which enables the mist quantity to be measured with high accuracy.

When the detection in the phototransistor 16 is emphasized, the light emitted by the light-emitting diode 15 has high energy if the wavelength thereof is less than 490 nm. If the wavelength is not less than 490 nm and not more than 550 nm, the visual confirmation is easy as described above.

An experiment was conducted using the mist measuring apparatus 100 according to the embodiment, in which an operation frequency of the metering pump 4 was varied in a range from 0.2 to 4.2 Hz by replacing three types of metering pumps 4 with different discharge capacities.

Figure 6:
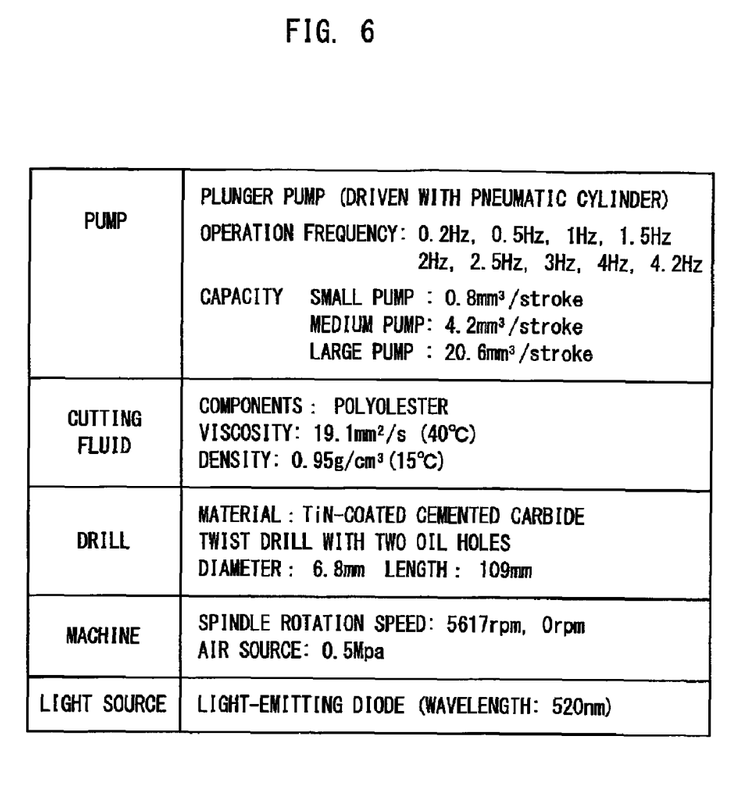
FIG. 6 shows experiment conditions in the first embodiment.

FIG. 6 shows experiment conditions in the first embodiment.

As shown in FIG. 6, the wavelength of the light-emitting diode 15 at the time of the experiment was 520 nm. The light was easily observed, and had relatively high energy.

A rotation speed of the drill was 5617 rpm in the case of detection by the phototransistor 16, and in the other case, it was 0 rpm.

As a result of visual observation, when the light source was OFF, or when the cutting fluid was not ejected (the mist 1 was ejected at 0 ml/h) even with the light source ON, the inside was observed to be in a dark state through the observation part 33. On the other hand, when the mist 1 was ejected at 15 ml/h, the inside was observed to be in a little lighter state through the observation part 33. Further, when the mist 1 was ejected at 75 ml/h, the whole inside was observed to be in a lighter state, in which the mist portion was extremely light and the ejection state of the mist 1 as indicated by hatching of FIG. 4 could be confirmed clearly.

Moreover, in an oscilloscope 27 shown in FIG. 1, a performance confirmation experiment of the mist measuring apparatus 100 was conducted by observing a signal of a pump drive command and an output signal of the phototransistor 16 after amplified by the amplifier 17.

Figure 7:
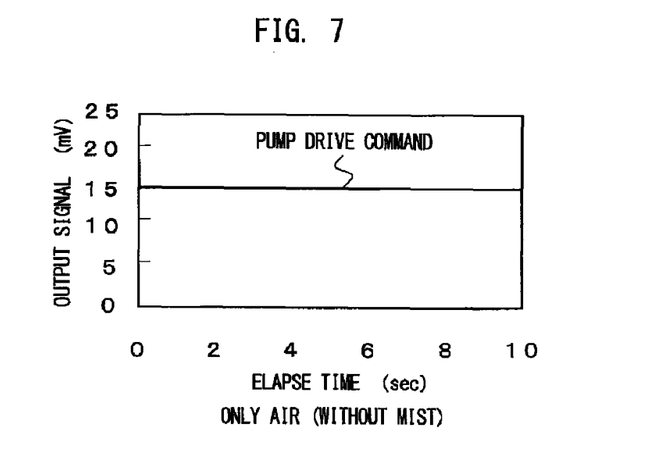
FIG. 7 shows a pump drive command for only air and measurement result of an output signal.
Figure 8:
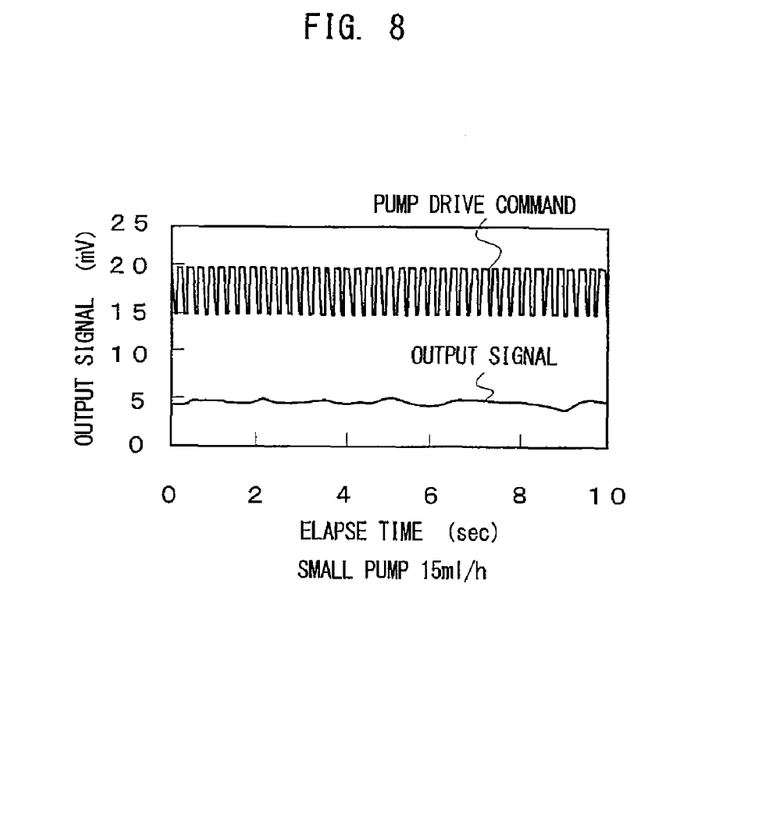
FIG. 8 shows a pump drive command when a small pump is used and measurement result of the output signal.
Figure 9:
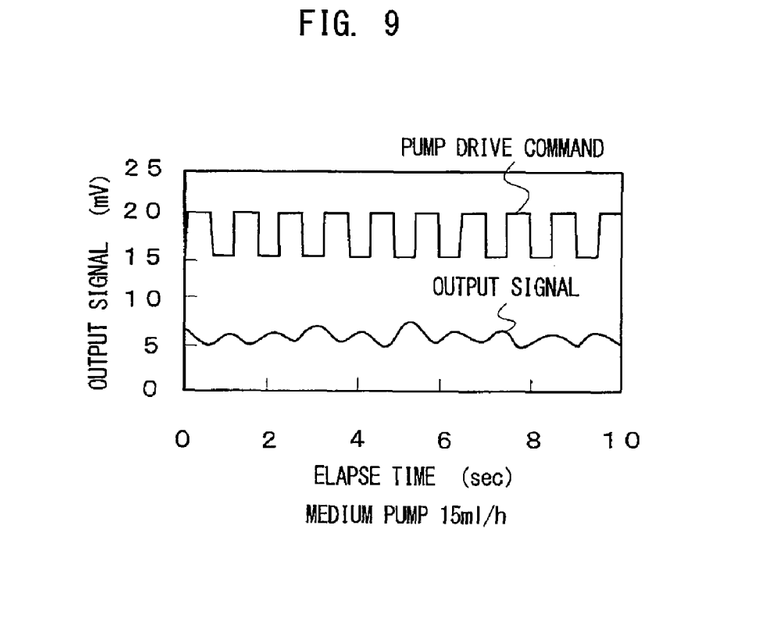
FIG. 9 shows a pump drive command when a medium pump is used and measurement result of the output signal.
Figure 10:
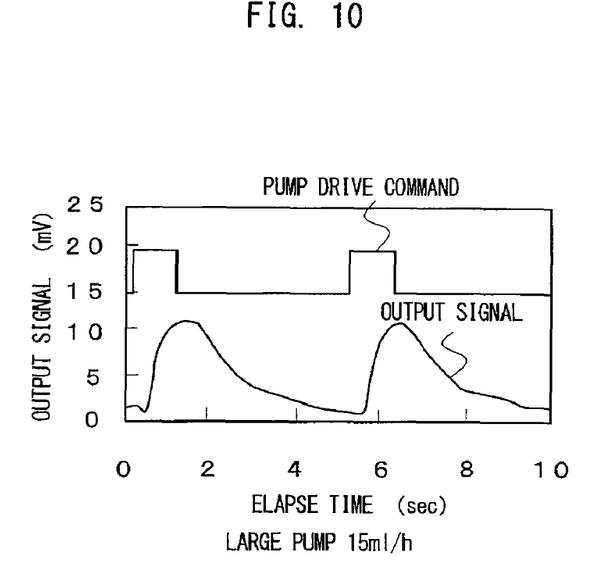
FIG. 10 shows a pump drive command when a large pump is used and measurement result of the output signal.

FIGS. 7 to 11 show the pump drive command and measurement result of the output signal. FIG. 7 shows a state where only air was ejected, FIG. 8 shows a case where the pump drive command was changed into a pulse shape using a small pump, FIG. 9 shows a case where the pump drive command was changed into a pulse shape using a medium pump, and FIG. 10 shows a case where the pump drive command was changed into a pulse shape using a large pump, respectively. Each supplied quantity of the cutting fluid 2 in FIGS. 8, 9, and 10 was 15 ml/h. In FIGS. 7 to 10, the pump drive command and the output signal of the phototransistor 16 (actually, output signal after amplified by the amplifier 17) are described in the same figures, respectively. However, in FIG. 7, the pump drive command was zero, and in FIGS. 8 to 10, even when the pump drive command was changed into a pulse shape, LOW of the pump drive command means zero.

As shown in FIG. 7, in the case where only the air is ejected without ejecting the mist 1, the output signal of the phototransistor 16 is zero. As shown in FIGS. 8, 9, and 10, in the case using any of the pumps, an average of the detected quantity is about 5 mV with respect to the ejected quantity of 15 ml/h, which means that the detected quantity follows the ejected quantity without being affected by the ejection pattern.

In this case, the ejection at 15 ml/h by the medium pump is a general condition adopted in normal MQL drill machining, and satisfies practicality.

Figure 11:
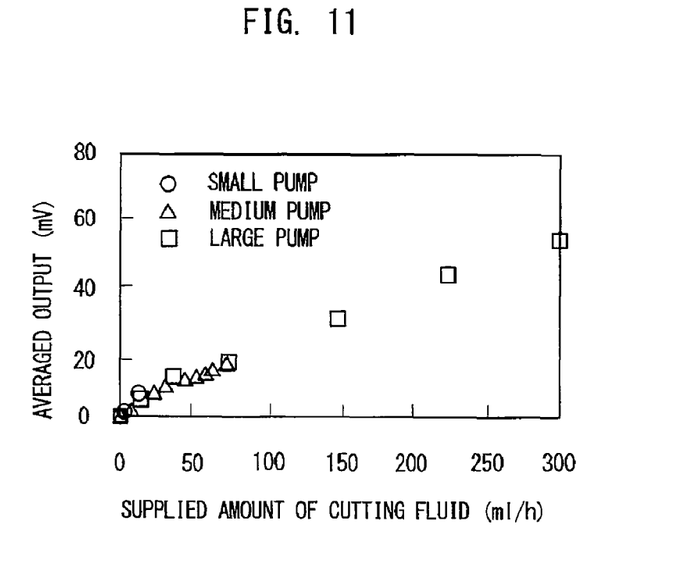
FIG. 11 is a chart showing a cutting-fluid supplied quantity and an average output signal.

FIG. 11 is a chart showing a cutting-fluid supplied quantity and an average output signal.

As shown in FIG. 11, even when the cutting-fluid supplied quantity is varied, a relationship with the average output is substantially linear, and a favorable result is obtained.

As described above, it was experimentally confirmed that by using the light scattering method, the ejection state of the mist 1 can be visually confirmed, and that the ejected quantity can be detected by the optical sensor. As a result, it was confirmed that the detection of the mist 1 by the light scattering method has sufficient practicality.

Figure 12:
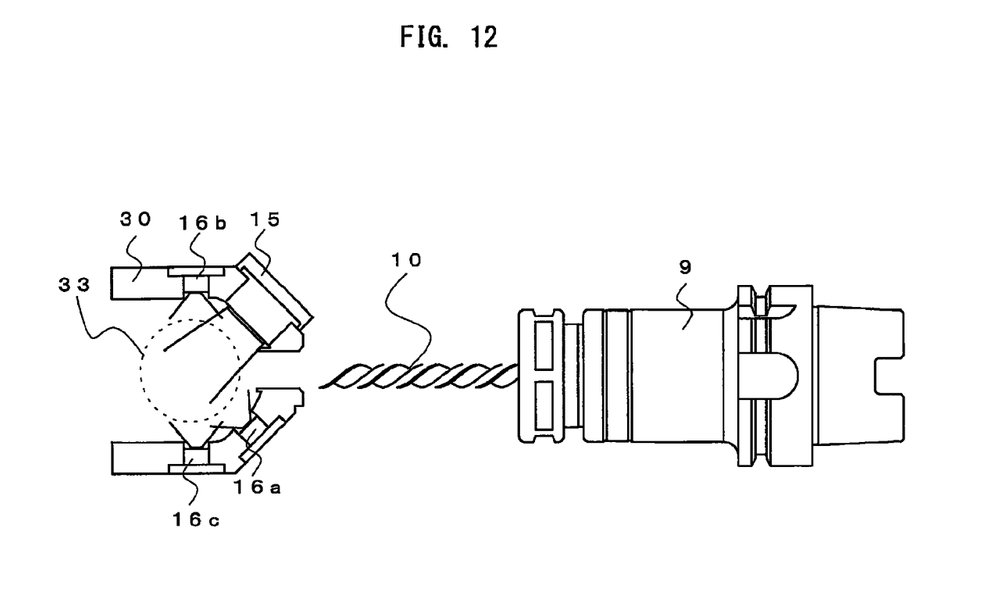
FIG. 12 is a view showing a mist measuring part according to a second embodiment.

FIG. 12 is a view showing a mist measuring part according to a second embodiment of the present invention.

In the second embodiment, the light-emitting diode 15 serving as the light source is arranged so as to emit light from an obliquely upper direction with respect to the ejection direction of the mist 1.

When the light is emitted from the light-emitting diode 15 in an oblique direction with respect to the mist 1, less outgoing light is blocked off by the tool 10, and the light goes across the whole mist, thereby increasing the scattered light in the mist 1.

Moreover, three phototransistors 16 serving as the optical sensors (16a to 16c) are provided, and one phototransistor 16a receives the light in a direction perpendicular to the emission direction of the light-emitting diode 15, and the other two phototransistors 16b and 16c are provided in an upper portion and a lower portion of the mist measuring part 11. In this manner, the provision of multiple phototransistors 16 increases the detectable scattered light, thereby increasing sensitivity of the mist measuring part 11, so that the state of the mist 1 can be detected with high accuracy. Moreover, since the scattered light is detected from multiple directions, the ejection state of the mist 1 can be grasped. In addition, the ejection state of the mist 1 can be visually confirmed through the observation part 33.

In this second embodiment as well, by utilizing the scattered light in the mist 1, the mist 1 can be visually confirmed and can be detected with high accuracy by the phototransistor 16.

Figure 13:
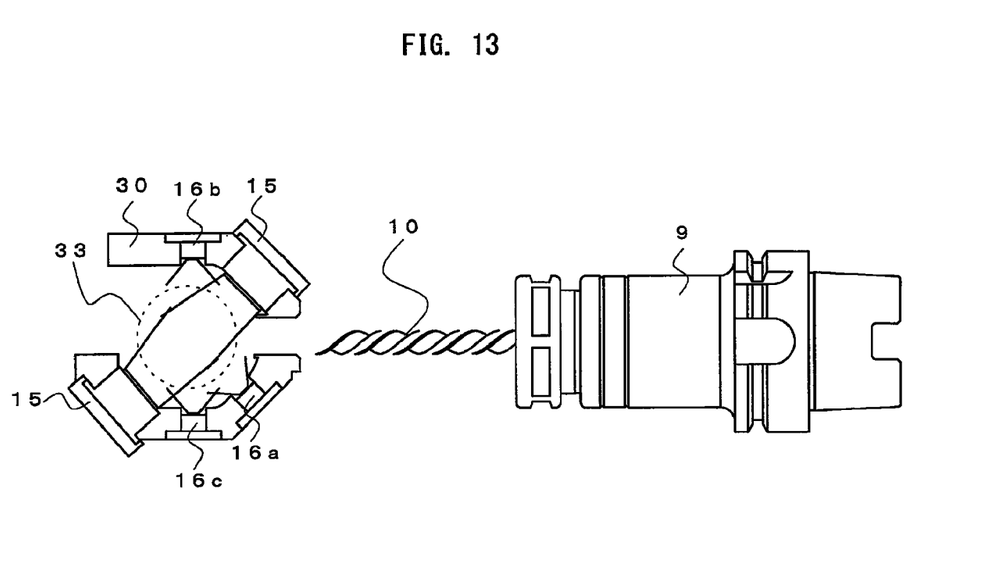
FIG. 13 is a view showing a mist measuring part according to a third embodiment.

FIG. 13 is a view showing a mist measuring part according to a third embodiment of the present invention.

In the third embodiment, two light-emitting diodes 15 emit light from an obliquely upper direction and from an obliquely lower direction with respect to the ejection direction of the mist 1. Similarly to the second embodiment, three phototransistors 16 are provided. The ejection state of the mist 1 can be visually confirmed through the observation part 33.

In this case, one of the wavelengths of the light-emitting diodes 15 is less than 490 nm. The light having a wavelength of less than 490 nm has high energy, which increases the sensitivity of the phototransistors 16.

The other light-emitting diode 15 is a light source emitting light having a wavelength of not less than 490 nm and not more than 810 nm, desirably substantially green light having a wavelength of not less than 490 nm and not more than 550 nm. In this manner, emitting the substantially green light increases the visual confirmation performance.

The present invention is not limited to the above-described embodiments.

The housing 30 does not need to have the shape and the arrangement as illustrated, as long as it functions as the dark room and the fixing member for the light source and the optical sensor. The function of the dark room and the function of the fixing member may be configured by different members. Similarly, the positions of the light source and the optical sensor can be modified.

Moreover, in the mist measuring part 11 in the first embodiment and second embodiment, in which only one light-emitting diode 15 is illustrated, a two-element incorporated light-emitting diode 15 having two wavelengths of the light easy to visually confirm and the light with high energy may be provided, or two light-emitting diodes 15 may be provided adjacent to each other in substantially the same position. As described above, as to the light source, the wavelength and the number thereof can be modified arbitrarily, as long as it is used so that a wavelength of a visible ray (wavelength of about 360 nm to about 810 nm, which differs among people), a wavelength making the visual confirmation easy, a wavelength with high energy (relatively short wavelength including a nonvisible ray such as an ultraviolet ray) are distinguished from one another.

The light-emitting diode 15 may be one element, a one-package product in which two elements are incorporated, two elements separately arranged, as described above, or otherwise three elements or four elements.

The optical sensor includes another optical sensor such as a photodiode, and a sensor for a nonvisible ray such as an ultraviolet sensor, as long as it can detect the scattered light, and the number thereof does not matter. Moreover, as to the observation part 33, the position and the shape thereof may be modified arbitrarily, as long as it is arranged in a position where the scattered light can easily be viewed.

In the above-described embodiments, while the mist ejection part 10a is provided at the front end of the tool 10, the mist 1 may be ejected from a different place from the tool 10.

REFERENCE SIGNS LIST 1 mist
2 cutting fluid
10 tool
10a ejection part
11 mist measuring part
15 light-emitting diode
16 phototransistor
26 mist adjustment part
30 housing
32 reflection preventer
32a reflecting surface
33 observation part
35 light receiving path tube
36 aspheric condenser lens
100 mist measuring apparatus

The invention claimed is:

1. A mist measuring apparatus comprising a housing, a light source that is provided in said housing and emits a visible ray to a misty cutting fluid, an optical sensor that is provided in said housing and receives scattered light from said misty cutting fluid, and an observation part that is provided in said housing and made up of a transparent window for observing said scattered light from said misty cutting fluid, in which said optical sensor is provided laterally to an optical path of outgoing light from said light source, and an ejected quantity of said misty cutting fluid is measured based on a quantity of received light in said optical sensor, wherein said housing is provided around an ejection part of said misty cutting fluid to block off outside light and make an inside thereof a dark room, a cylindrical reflection preventer is provided ahead of said light source to prevent said outgoing light from reaching directly to said observation part and said optical sensor, a cylindrical light receiving path tube is provided ahead of said optical sensor, projecting toward the optical path of said outgoing light to make less outgoing light enter said optical sensor, and said scattered light passes through said light receiving path tube and is received by said optical sensor.

2. The mist measuring apparatus according to claim 1, wherein the light emitted from said light source is a substantially green visible ray, having a wavelength of not less than 490 nm and not more than 550 nm.

3. The mist measuring apparatus according to claim 1, wherein said optical sensor is plurally provided.

4. The mist measuring apparatus according to claim 1, wherein a collecting lens is provided between said optical sensor and said light receiving path tube, and said scattered light passes through said light receiving path tube to be collected by said collecting lens and is received by said optical sensor.

5. The mist measuring apparatus according to claim 1, further comprising;

a light source that emits a light with high energy having a wavelength of less than 490 nm, and a light source that emits a visible ray having a wavelength of not less than 490 nm and not more than 810 nm.

6. The mist measuring apparatus according to claim 1, further comprising:

a light source that emits a light with high energy having a wavelength of less than 490 nm, and a light source that emits a substantially green visible ray having a wavelength of not less than 490 nm and not more than 550 nm.

* * * * *